United States Patent
Mori et al.

(10) Patent No.: US 7,018,586 B2
(45) Date of Patent: *Mar. 28, 2006

(54) WEATHERING TEST APPARATUS

(75) Inventors: Kanji Mori, Aichi (JP); Takeshi Narita, Aichi (JP); Kazuo Okamoto, Aichi (JP); Masao Tsuji, Aichi (JP); Kazuyuki Tachi, Aichi (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 313 days.

This patent is subject to a terminal disclaimer.

(21) Appl. No.: 10/640,396

(22) Filed: Aug. 14, 2003

(65) Prior Publication Data

US 2004/0031336 A1 Feb. 19, 2004

Related U.S. Application Data

(60) Continuation of application No. 10/201,256, filed on Jul. 24, 2002, now Pat. No. 6,709,631, which is a division of application No. 09/398,823, filed on Sep. 20, 1999, now Pat. No. 6,682,932.

(30) Foreign Application Priority Data

Sep. 24, 1998 (JP) .................................. 10-269576
Oct. 9, 1998 (JP) .................................. 10-288349

(51) Int. Cl.
G01N 17/00 (2006.01)
(52) U.S. Cl. .............................. 422/53; 422/102; 436/6; 436/135; 436/165; 73/DIG. 10
(58) Field of Classification Search ................ 436/1–6, 436/135, 166, 167; 422/53, 102, 99; 73/DIG. 10

See application file for complete search history.

(56) References Cited

U.S. PATENT DOCUMENTS

| | | | |
|---|---|---|---|
| 3,488,681 A | 1/1970 | Mita et al. | |
| 3,501,942 A | 3/1970 | Fitzgerald et al. | |
| 3,664,188 A | 5/1972 | Kockott | |
| 4,600,695 A | 7/1986 | Cummings et al. | |
| 4,874,952 A | 10/1989 | Arnaud et al. | |
| 5,098,848 A | 3/1992 | Kley et al. | |
| 5,215,192 A | 6/1993 | Ram et al. | |
| 5,948,484 A | 9/1999 | Gudimenko et al. | |
| 6,709,631 B1 * | 3/2004 | Mori et al. | 422/53 |

FOREIGN PATENT DOCUMENTS

| | | |
|---|---|---|
| DE | 1598811 | 10/1970 |
| GB | 1226956 | 3/1971 |
| JP | 09-119893 | 5/1967 |
| JP | 48-60695 | 11/1971 |
| JP | 57014740 A | 1/1982 |

(Continued)

*Primary Examiner*—Lyle A. Alexander
(74) *Attorney, Agent, or Firm*—Oblon, Spivak, McClelland, Maier & Neustadt, P.C.

(57) ABSTRACT

A weathering test method comprising making active oxygen and light simultaneously act on a test piece, a weathering test method comprising successive and/or alternate steps of making active oxygen and light simultaneously act on a test piece and making at least one of light, oxygen, and water to act on the test piece, and apparatus for carrying out the methods are disclosed. In evaluating weatherability of organic materials, articles made of organic materials or articles coated with organic materials, the methods and apparatus achieve acceleration of deterioration of test pieces to greatly reduce the testing time.

19 Claims, 7 Drawing Sheets

| FOREIGN PATENT DOCUMENTS | | | JP | 61083947 A | 4/1986 |
|---|---|---|---|---|---|
| | | | JP | 63-222240 | 9/1988 |
| JP | 1-28897 | 12/1982 | JP | 09320403 A | 12/1997 |
| JP | 57211528 A | 12/1982 | | | |
| JP | 2-1259 | 8/1983 | * cited by examiner | | |

WEATHERING TEST APPARATUS

FIELD OF THE INVENTION

This invention relates to a test method for evaluating weatherability of articles and materials thereof and an apparatus for carrying out the test. More specifically, the invention is applied to a weatherability test of organic materials, articles made of the organic materials, articles coated with the organic materials, and the like which are used outdoors.

BACKGROUND OF THE INVENTION

Weathering tests designed to evaluate weatherability of organic materials such as coatings include an outdoor exposure test in which a test piece is exposed to the weather and a traced and collected sunlight exposure test in which a test piece is exposed to traced and collected sunlight. In addition, special test methods include an artificial accelerated weathering test in which a test piece is irradiated with light from an artificial light source by means of a weathering apparatus, such as a sunshine weather meter, a UV carbon weatherometer, a xenon weatherometer, a dew panel weatherometer, and a metal halide weatherometer.

JP-A-48-60695 discloses a method for accelerating a salt spray test for evaluating anticorrosion of steel stock against seawater, in which hydrogen peroxide-added salt water is used as testing seawater.

The above-mentioned outdoor exposure test and traced and collected sunlight exposure test require an extremely long period of time not shorter than several months for test pieces to be deteriorated. It has been impossible with these weathering tests to evaluate weatherability rapidly.

The problem of the artificial accelerated weathering test, on the other hand, is that the test fails to sufficiently reproduce the deterioration that should have been resulted from exposure to natural weathering conditions. That is, the deteriorated state of a test piece does not agree with that in the outdoors for the following reason. When articles or materials are long-term exposed outdoors, their deteriorated surface, typically the coating film, shows a surface profile with fine waviness and fine pits in a mixed state, both of which reduce the surface gloss, whereas the surface profile developed in the accelerated weathering test mainly displays fine waviness so that the reduction in gloss as observed is chiefly ascribed to the fine waviness alone.

The above-described improved salt spray test aims at acceleration of a durability test, but its application is limited to evaluation of anticorrosion of steel stock against seawater in special fields. It does not apply to weatherability testing of organic materials or articles thereof.

SUMMARY OF THE INVENTION

An object of the present invention is to provide a test method and an apparatus for evaluating weatherability of organic materials, articles made of organic materials, and materials coated with organic materials in an accelerated manner to greatly reduce the testing time.

Another object of the invention is to provide a weathering test method and an apparatus therefor which greatly speed up deterioration of a test piece while achieving satisfactory reproduction of outdoor deterioration.

The invention relates to a weathering test method and a weathering apparatus for evaluating weatherability of a test piece such as an organic material, an article made of an organic material or an article coated with an organic material.

The invention provides in its first aspect a weathering test method comprising making active oxygen and light simultaneously act on a test piece and evaluating the resultant deterioration, and a weathering apparatus used to carry out the test method.

The invention provides in its second aspect a weathering test method comprising successive and/or alternate steps of making active oxygen and light simultaneously act on a test piece and making at least one of light, oxygen, and water to act on the test piece, and a weathering apparatus used to carry out the test method.

BRIEF DESCRIPTION OF THE INVENTION

Figure 3:
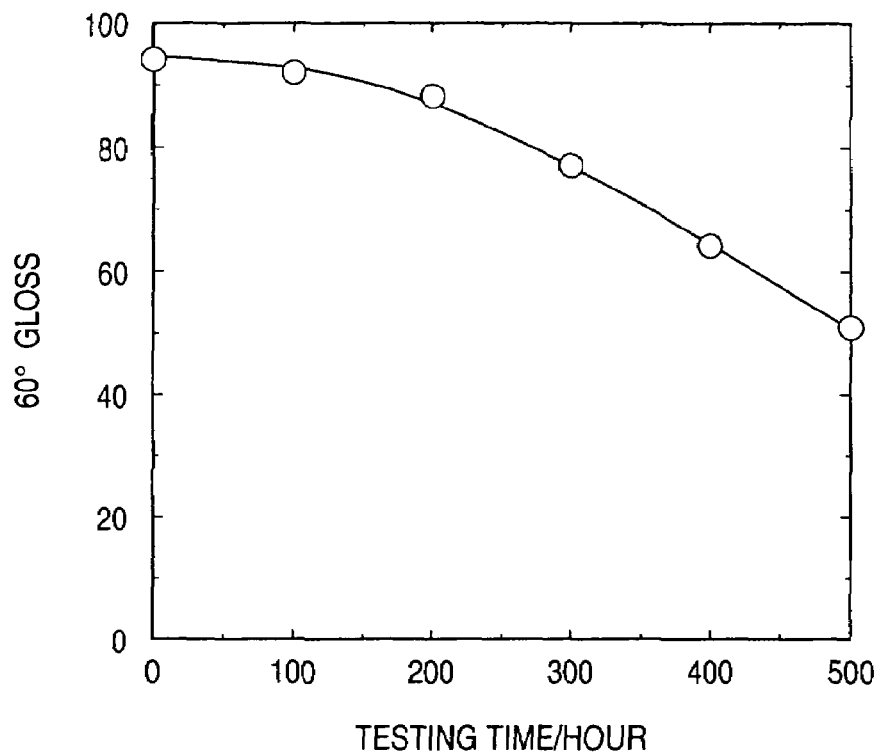

FIG. 3 displays the relationship between testing time and 60° gloss in Example 4.

Figure 4:
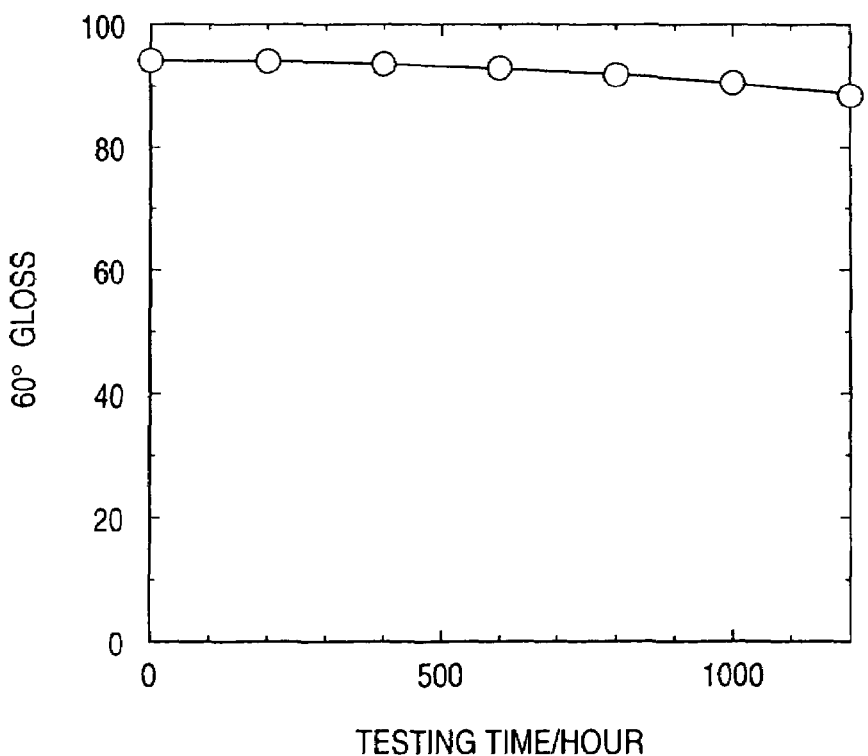

FIG. 4 depicts the relationship between testing time and 60° gloss in Comparative Example 3.

Figure 5:
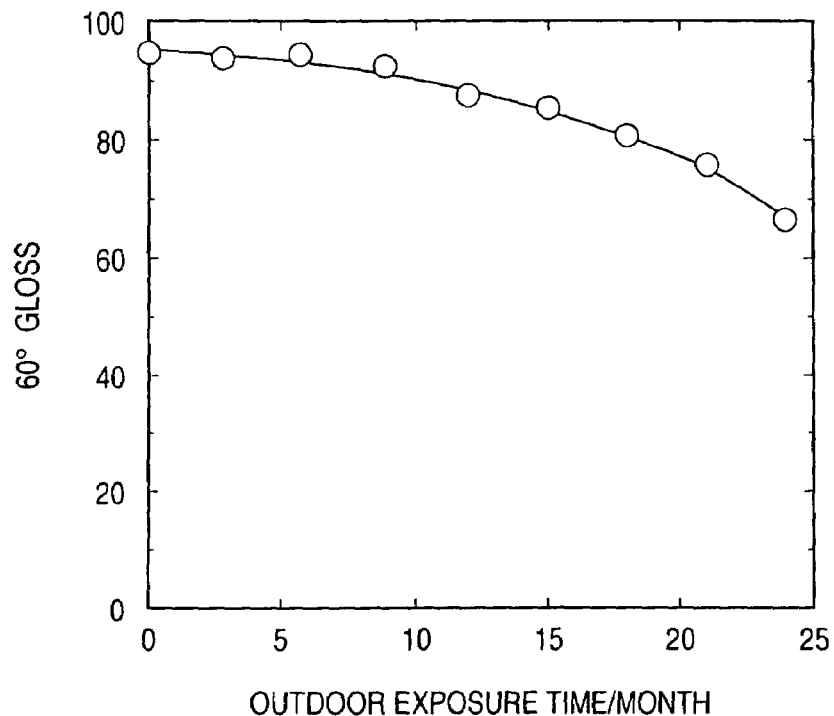

FIG. 5 shows the relationship between outdoor exposure time and 60° gloss in Comparative Example 4.

Figure 6:
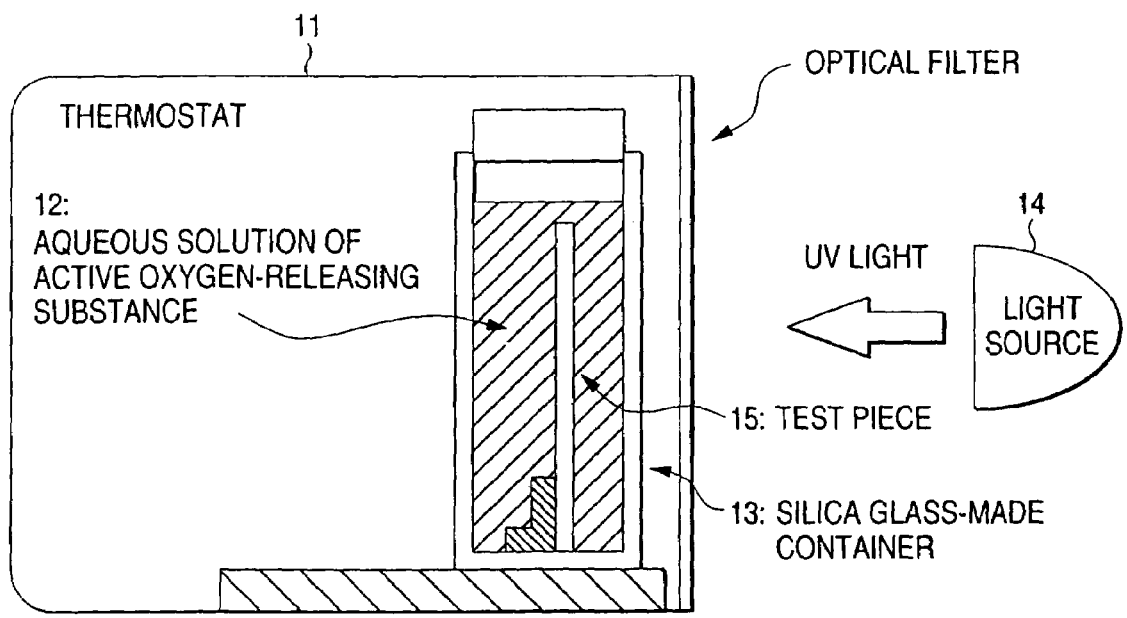

FIG. 6 is a schematic illustration of a weathering apparatus according to the invention.

Figure 7:
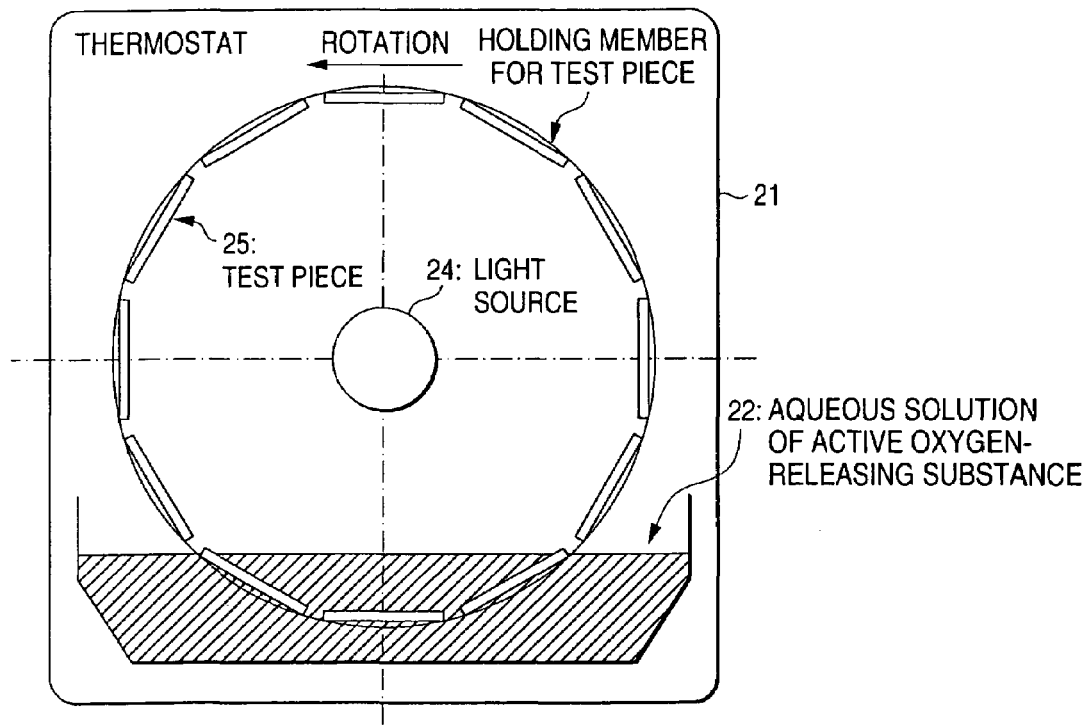

FIG. 7 schematically illustrates another weathering apparatus according to the invention.

Figure 8:
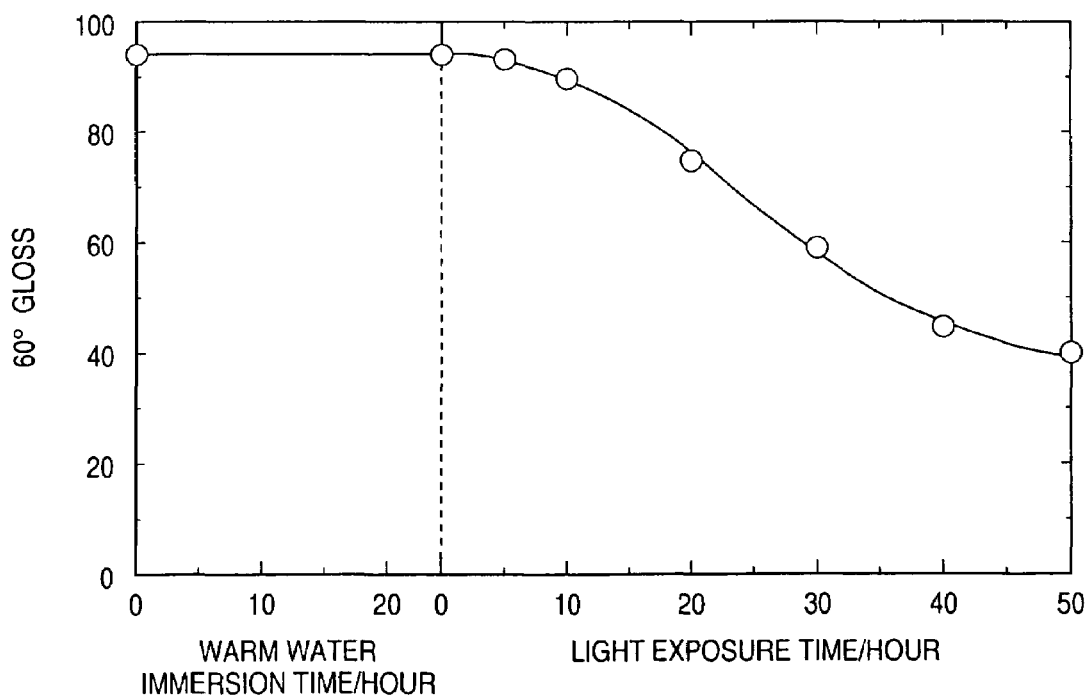

FIG. 8 is a graph of warm water immersion time and light exposure time vs. 60° gloss in Example 7.

Figure 9:
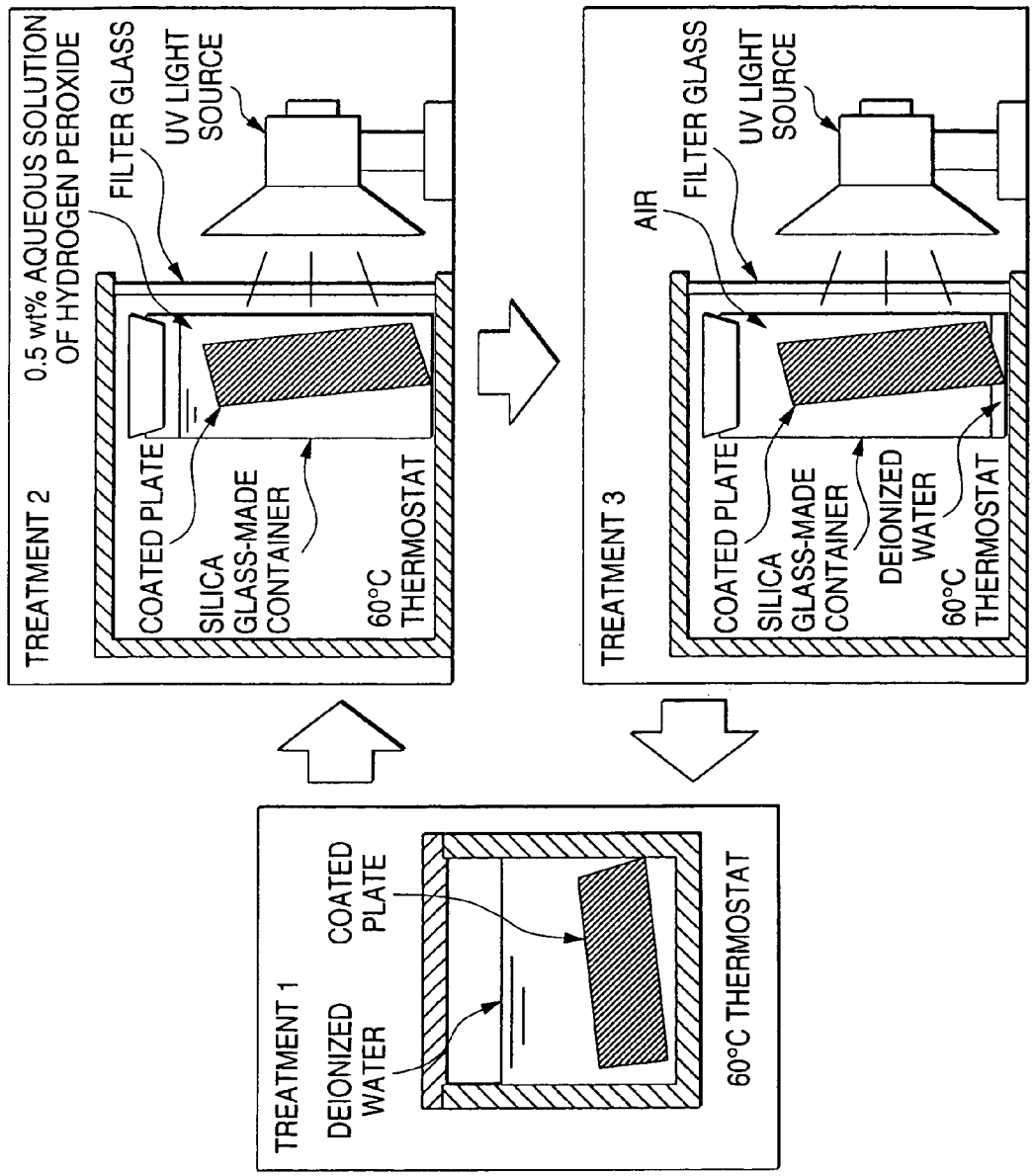

FIG. 9 is an illustration showing the cycle of treatments in Example 8 and the apparatus therefor.

Figure 10:
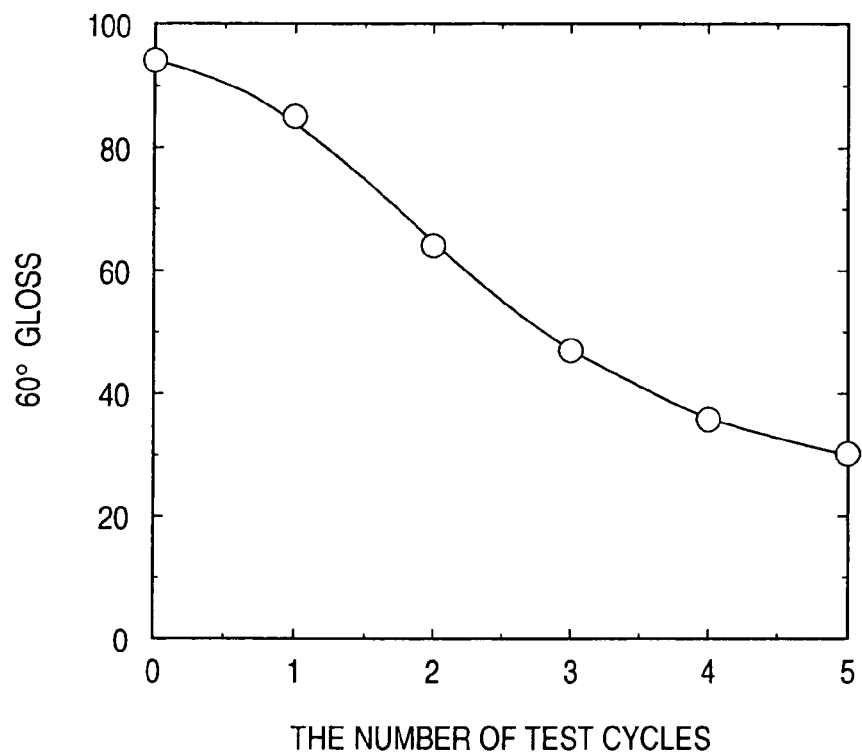

FIG. 10 depicts the relationship between 60° gloss and the number of test cycles in Example 8.

Figure 11:
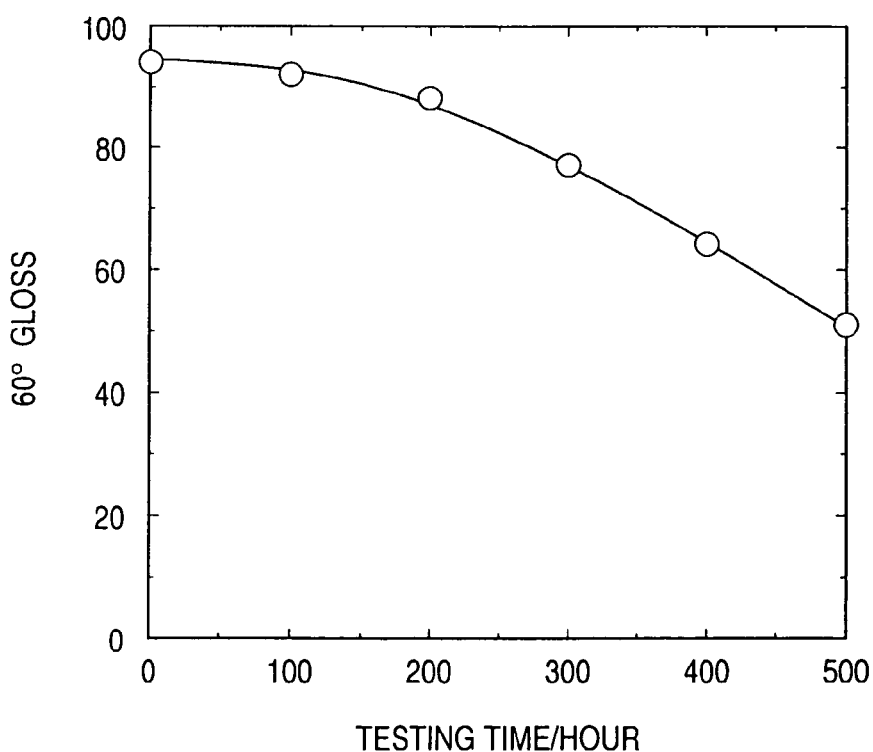

FIG. 11 shows the relationship between testing time and 60° gloss in Example 9.

Figure 12:
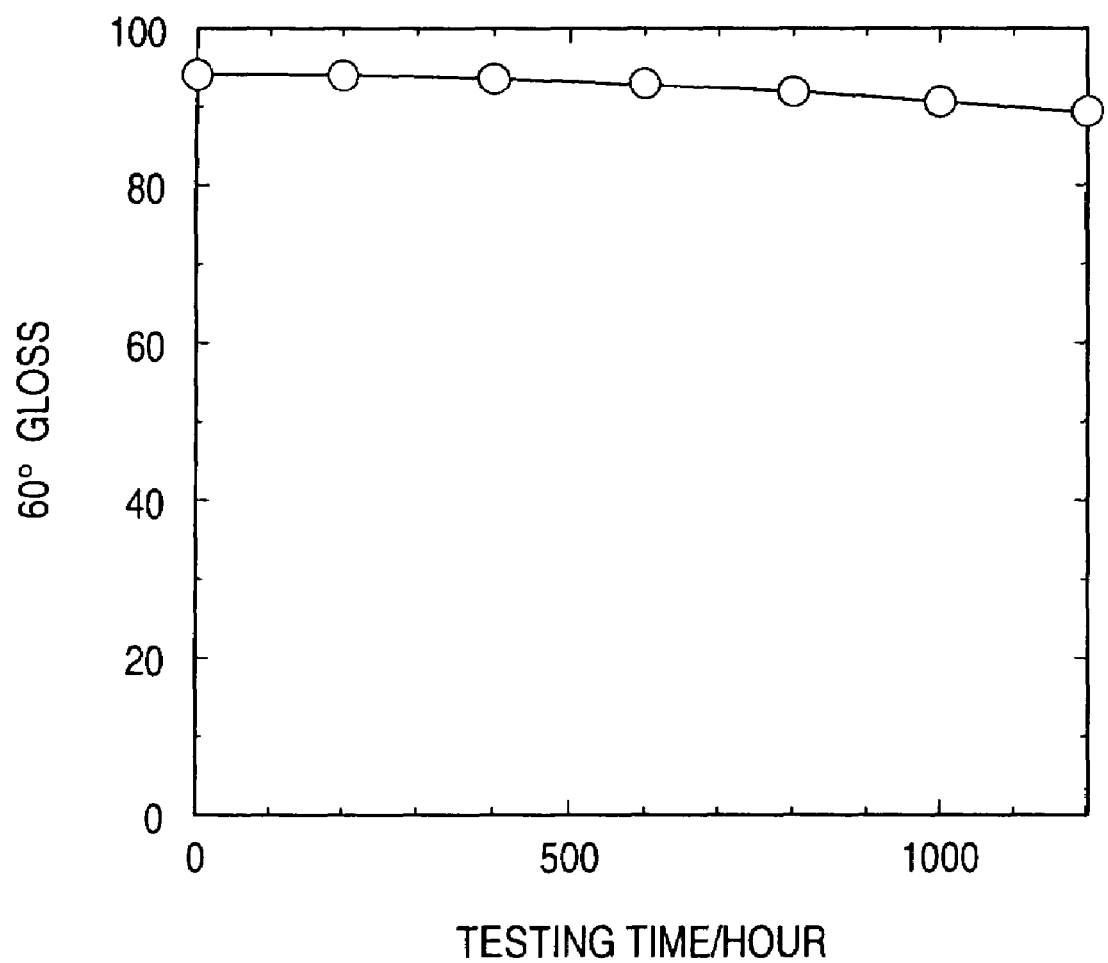

FIG. 12 displays the relationship between testing time and 60° gloss in Comparative Example 8.

DETAILED DESCRIPTION OF THE INVENTION

The weathering test according to the first aspect of the invention is characterized in that active oxygen is made to act on a test piece simultaneously with irradiation.

Deterioration of materials is in general a phenomenon that the material absorbs light energy to become an active species, which reacts with oxygen in the atmosphere to undergo chemical denaturation. According to the invention, the above-mentioned chemical reaction is accelerated by making light and active oxygen simultaneously act on a test piece to markedly speed up the deterioration phenomenon of the test piece and thereby greatly shortening the time required for testing.

In the practice of the weathering test according to the first aspect of the invention, active oxygen can be made to act on a test piece either directly or indirectly. The case where active oxygen is made to act on the test piece indirectly is preferred to the case where active oxygen is made to act on the test piece directly.

For example, in a preferred embodiment, active oxygen is allowed to directly act on a test piece by bringing active oxygen into direct contact with a test piece. This can be achieved by subjecting a test piece to an oxygen plasma treatment.

Considering that active oxygen is difficult to handle in storing or weighing because of its high reactivity, it is another preferred embodiment that active oxygen is allowed to act indirectly on a test piece by bringing a substance capable of releasing active oxygen (hereinafter referred to as an active oxygen-releasing substance) into contact with a test piece. The active oxygen-releasing substance includes oxidizing agents containing oxygen. Oxidizing agents containing oxygen include hydrogen peroxide, ozone, peracids, peracid salts, hypohalogenous acids, and hypohalogenous acid salts. Hydrogen peroxide is preferred. The contact between the test piece and the active oxygen-releasing substance may be either directly or indirectly. The direct contact can be made by, for example, coating the test piece with a liquid active oxygen-releasing substance.

However, where the oxygen-releasing substance is brought into direct contact with a test piece, it is difficult to control the action of released active oxygen on the test piece, which will limit the applicability of the test method. Therefore, it is still another preferred embodiment that the active oxygen-releasing substance is brought into indirect contact with a test piece by using a water-soluble active oxygen-releasing substance in the form of its aqueous solution. Of the above-described active oxygen-releasing substances, water-soluble ones include hydrogen peroxide and hypohalogenous acid salts. An aqueous solution of hydrogen peroxide (hereinafter referred to as aqueous hydrogen peroxide) is particularly preferred. In this preferred embodiment using the active oxygen-releasing substance in aqueous solution, deterioration is accelerated easily, and the concentration of the oxidizing agent is easily controllable, making it easy to control the speed of deterioration.

The contact of the aqueous solution of the active oxygen-releasing substance is preferably achieved by (i) immersing the test piece in the aqueous solution or (ii) dropping or spraying the aqueous solution onto the test piece.

It is also still another preferred embodiment that the active oxygen-releasing substance is brought into indirect contact with a test piece by (iii) penetrating the active oxygen-releasing substance into the test piece and letting the substance release active oxygen inside the test piece. In this case, too, hydrogen peroxide is preferably used as an active oxygen-releasing substance.

The water-soluble active oxygen-releasing substance includes hydrogen peroxide and hypohalogenous acid salts. Hydrogen peroxide is particularly preferred for its high reactivity, i.e., high capability of accelerating deterioration. In using hydrogen peroxide in aqueous solution, an effective concentration ranges from 0.001 to 60% by weight, preferably from 0.01 to 10% by weight. In concentrations lower than 0.001%, the degree of deterioration acceleration tends to be insubstantial for achieving the effects as expected in the invention. Concentrations exceeding 60% tend to cause deterioration too rapidly to stop the deterioration reaction under proper treating conditions, which will impair the accuracy of the test. With the concentration falling within the preferred range of from 0.01 to 10%, reproducibility of the test can be secured, and the test can be accomplished in a short time with improved accuracy.

Where hydrogen peroxide is used in the form of an aqueous solution which is brought into contact with a test piece or where hydrogen peroxide is penetrated into a test piece, it is desirable that the test piece be kept at 0 to 120° C. At the test piece's temperature lower than 0° C., the degree of deterioration acceleration tends to be insufficient for manifesting the effects of the invention as expected. At the test piece's temperature higher than 120° C., cases are sometimes met with, in which some chemical reaction that would not take place outdoors may occur, failing to achieve the object of the test.

According to the first aspect of the invention, a test piece is irradiated with light while receiving the action of active oxygen. Light to be used is not particularly limited as long as it has energy to activate the material making up the test piece. Because many of industrially important materials mutually react with light having wavelengths not more than 400 nm, it is desirable for the irradiating light to contain light rays having wavelengths of 400 nm or less. Any light source that has been employed in conventional weathering tests can be adopted in the present invention. Suitable light includes not only sunlight but light from artificial light sources, such as a xenon lamp, a metal halide lamp, a carbon arc lamp, and a UV fluorescent lamp, and a combination thereof. If necessary, an appropriate optical filter can be used in combination.

The weathering test according to the first aspect of the invention is preferably carried out by means of a weathering apparatus comprising a thermostat in which a test piece is put, a means for making active oxygen act on the test piece in the thermostat, and a means for making light act on the test piece. Preferred examples of the apparatus will be described in detail in Examples hereinafter given.

The language "making active oxygen and light simultaneously act on a test piece" as used herein means that irradiation may not be necessarily made to act on a test piece simultaneously with a treatment using an oxidizing agent, provided that light is made to act on the test piece in the presence of the active oxygen.

The weathering test method according to the second aspect of the invention comprises a first step of making active oxygen and light simultaneously act on a test piece and a second step of making at least one of light, oxygen, and water to act on the test piece, the first and the second steps being performed successively and/or alternately.

In general, outdoor deterioration of materials and articles made of the materials (hereinafter inclusively referred to as material (s)) is a phenomenon that the material undergoes chemical denaturation by the actions of water, oxygen and light in the environment. Of these actions, the action of water is to cause hydrolysis to degrade part of the material to low-molecular substances and to remove the low-molecular substances from the surface through extraction and vaporization. As a result, fine waviness develops on the surface of the material. When this happens on, for example, a resin-coated article, the resin except for pigments shrinks, and fine waviness of the surface results to reduce the surface gloss.

The action of light is to give light energy to the material to make it an active species, which reacts with oxygen in the atmosphere to form and/or sever various chemical bonds. By this action of light, part of the material is denatured into low-molecular substances, which are extracted and vaporized from the surface to develop fine waviness on the surface.

Further, in the case of coating materials comprising resins and pigments and articles coated therewith, some pigments have photocatalysis to accelerate local deterioration around the pigment particles. One of the characteristics of the surface profile observed in this case is that the resin around the pigment particles in the vicinities of the surface is lost to leave fine pits on the surface. These pits as well as the fine waviness reduce the gloss of the coating film.

In fact, close examination of the surface profile of a coating film having deteriorated by outdoor exposure usually reveals fine waviness and fine pits in a mixed state. This indicates that the weathering action produces both fine waviness and fine pits. Therefore, in order to reproduce weathering deterioration in an accelerated manner, it is necessary to accelerate at least one of the actions of water and of light causing fine waviness and also the action of light causing fine pits. From this viewpoint, the conventional accelerated weathering tests fail to reproduce outdoor deterioration and are inadequate as a test aiming at reproduction of outdoor deterioration.

In this regard, the weathering test according to the second aspect of the invention achieves acceleration and reproduction of the outdoor deterioration that could not be reproduced in the conventional accelerated weathering tests while properly balancing the above-mentioned various actions. That is, the weathering test is to reproduce the surface profile of the material, for example, a coating film having deteriorated by outdoor exposure.

In detail, the first step is to accelerate deterioration by making both active oxygen and light to act on a test piece to develop fine pits as observed in outdoor deterioration. For example, some pigments contained in the resin coating film exert photocatalysis to induce an oxidation reaction around the pigment particles as mentioned above. It follows that the resin is lost to leave fine pits in an accelerated manner. In the second step, on the other hand, fine waviness develops on the surface of the test piece thereby achieving accelerated deterioration. Specifically, where water is made to act, the coating film, etc. are partially hydrolyzed with water and degraded into low-molecular substances, which are lost through extraction or vaporization. It follows that the coating film, etc. shrink to develop fine waviness on the surface thereby to accelerate deterioration. Where light is allowed to act, low-molecular substances are produced by an oxidation reaction in which light participates, and the low-molecular substances are lost due to extraction or vaporization to produce fine waviness similarly. Where oxygen is made to act, low-molecular substances are produced by an oxidation reaction, which similarly results in fine waviness. Combination of the first and the second steps produces both fine pits and waviness that would have developed in outdoor exposure to accelerate deterioration, whereby outdoor deterioration can be reproduced.

The language "making active oxygen and light simultaneously act on a test piece" as used herein means that irradiation may not be necessarily made to act on a test piece simultaneously with a treatment using an oxidizing agent, provided that light is made to act on the test piece in the presence of the active oxygen.

The language "successive and/or alternate steps" as used herein means that the first step, taken as step A, and the second step, taken as step B, can be combined in the order of A-B, B-A, A-B-A-B . . . , A-B1-B2-A-B1-B2 . . . , and the like, wherein B1 and B2 are different treatments included in step B as hereinafter described in detail. In what follows, the first and the second steps will sometimes be referred to as step A and step B, respectively.

Step A is a step of making active oxygen and light simultaneously act on a test piece to accelerate and reproduce the deteriorating action causing fine pits, which is one of the deteriorating actions in which light takes part. In order to make active oxygen to act, an oxidizing agent is used as an active oxygen-releasing substance. The oxidizing agent to be used is preferably selected from hydrogen peroxide, ozone, peracids, peracid salts, hypohalogenous acids, hypohalogenous acid salts, and chlorine. Hydrogen peroxide is particularly preferred. Other known oxidizing agents are also employable. The oxidizing agent selected is used in aqueous solution. The oxidizing agent can be allowed to act on a test piece by immersing the test piece in the aqueous solution of the oxidizing agent or dropping or spraying the aqueous solution onto the test piece so that the aqueous solution may run thereon. Step A may also be effected in an embodiment wherein the oxidizing agent is made to penetrate into the test piece by the above-described manner and, after the aqueous solution is removed by, for example, washing with water, the test piece is irradiated with light to make the oxidizing agent and light act simultaneously.

Where a test piece is, for example, a coated article, the treatment with active oxygen and light in step A results in development of fine pits on the surface of the coating film. This deteriorated state is chiefly attributed to the oxidation reaction caused by the oxidizing agent and light acting substantially simultaneously. Depending on the oxidizing agent selected, the oxidation reaction causes an oxygen element to bind to the test piece or causes an element other than oxygen to bind to the test piece. In general, the oxidation occurring on organic materials used outdoors to cause deterioration is a reaction of oxygen element's binding to the test piece. In order to reproduce outdoor weathering deterioration, an oxidation reaction in which an oxygen element participates should take place.

In case where step A is undertaken by using an oxidizing agent which involves an oxidation reaction in which an oxygen element participates, it is possible to cause an oxidation reaction with oxygen in step A alone. Where such an oxidizing agent is not chosen, an oxidation reaction with oxygen does not occur in step A. In this case, however, it is possible to induce elements replacement to cause an oxidation reaction with oxygen by properly selecting the treatment to be undertaken in the following step B. In this case step B is required to comprise a means for allowing at least oxygen to act.

Step B is to make at least one of water, oxygen, and light to act on the test piece. Step B specifically includes the following treatments B1 to B6.

Treatment B1: immersing a test piece in warm water. The temperature of the warm water for the warm water immersion as used herein is from about 30° C. to about 100° C.

Treatment B2: immersing a test piece in warm water while irradiating.

Treatment B3: the treatment B2 in which the warm water contains dissolved oxygen in equilibrium with an oxygen partial pressure of 0.2 atm or more.

Treatment B4: irradiating a test piece in a gas containing steam.

Treatment B5: the treatment B4 in which the gas further contains 0.2 atm or more of oxygen.

Treatment B6: a treatment according to a conventional weathering test involving water as a load factor. The conventional weathering test useful in treatment B6 includes an outdoor exposure test, a traced and collected sunlight exposure test, and an artificial accelerated weathering test using various artificial light sources.

Light to be used in steps A and B is not particularly limited as long as it has energy to activate the material making up the test piece. Because many of industrially important materials mutually react with light having wavelengths not more than 400 nm, it is desirable for the irradiating light to contain light rays having wavelengths of 400 nm or less. Any light source that has been employed in conventional weathering tests can be adopted. Suitable light includes not only sunlight but light from artificial light sources, such as a xenon lamp, a metal halide lamp, a carbon arc lamp, and a UV fluorescent lamp, and a combination thereof. If necessary, an appropriate optical filter can be used in combination.

Where step B is performed in an artificial environment, it is desirable that the test piece be kept at 0 to 120° C. At the test piece's temperature lower than 0° C., the degree of deterioration acceleration tends to be insufficient for manifesting the effects of the invention as expected. At the test piece's temperature higher than 120° C., some chemical reaction that would not take place outdoors tends to occur, failing to obtain the effects as aimed.

Where the test piece is, for example, a coated article, the deterioration accelerated in step B results in development of fine waviness on the surface of the coating film.

The above-described weathering test according to the second aspect of the invention is preferably carried out by means of a weathering apparatus comprising a container in which a test piece is put, a means for making active oxygen and light simultaneously act on the test piece, and a means for making at least one of water, oxygen, and light act on the test piece.

Where a test piece is irradiated with light through the wall of the container in which the test piece is placed, the container should be made of a light-transmitting material. In using light containing UV rays, a material transmitting UV rays, such as silica glass, is preferred.

The means for making active oxygen and light simultaneously act on the test piece includes a means for irradiating the test piece as immersed in an aqueous solution of the oxidizing agent. It is preferred for the apparatus to have a function for maintaining the temperature inside the container constant so that the rate of deterioration may be adjusted. A temperature control unit is an effective means for maintaining the temperature inside the container constant.

The light source may be either the sun or an artificial light source. An artificial light source is preferably incorporated into the apparatus. Any known light sources used in conventional artificial accelerated weathering tests can be utilized, including a xenon lamp, a metal halide lamp, and a UV fluorescent lamp. To control the spectral distribution of the light from these light sources, it is advantageous to provide an appropriate optical filter between the light source and the test piece.

The means for making at least one of water, oxygen, and light act on the test piece includes conventional means employed in an outdoor exposure test, a traced and collected sunlight exposure test, and an artificial accelerated weathering test using various artificial light sources and the same means as used in step A for making an oxidizing agent aqueous solution and light act on a test piece substantially simultaneously except that the oxidizing agent aqueous solution is replaced with pure water, air containing steam, and the like.

In a preferred embodiment of the apparatus, a test piece is put in a container made of silica glass, and the container is set in a thermostat. The wall of one side of the thermostat is made of a plate of silica glass or of glass which also functions as an optical filter. The test piece is irradiated with light emitted from an artificial light source, such as a xenon lamp, a metal halide lamp, and a UV fluorescent lamp, through the glass plate and the wall of the silica glass-made container.

The silica glass-made container has an opening at its bottom, the opening connected through piping to an external apparatus from which liquid or gas is introduced into the container in accordance with programmed timing. The substance introduced into the container through this opening and piping includes an aqueous solution of hydrogen peroxide in step A and pure water, air at controlled temperature and humidity, and a special mixed gas having an oxygen partial pressure increased over that of air in step B. The test is carried out automatically according to programmed timing.

The present invention will now be illustrated in greater detail with reference to Examples in view of Comparative Examples, but it should be understood that the invention is not construed as being limited thereto. In Examples and Comparative Examples, aqueous hydrogen peroxide was used in a prescribed concentration as diluted a 30 wt % reagent of aqueous hydrogen peroxide (available from Wako Pure Chemical) with ion-exchanged water.

EXAMPLE 1

A steel plate (7 cm×15 cm×0.8 mm) was subjected to electrodeposition, and a primer and a topcoat of white paint were applied to prepare a coated plate as a test piece. Sodium hypochlorite hexahydrate (produced by Wako Pure Chemical Industries, Ltd.), which is a liquid substance, was uniformly applied to the coated side of the plate in an amount of 0.5 g/side. The plate was set to stand still in a thermostat kept at 40° C. and irradiated with light from a UV fluorescent lamp about 60 mm away from the plate for 10 hours. An optical filter was placed between the coated plate and the light source so that the light reaching the coated plate might have wavelengths of 295 to 400 nm.

After the irradiation, the coated plate was washed with water and dried, and gloss at 60° was measured with a glossmeter GM-3D (manufactured by Murakami Color Research Laboratory). The 60° gloss of the plate immediately after the preparation was 94, whereas that after the test was 75.

COMPARATIVE EXAMPLE 1

A plurality of coated plates prepared in the same manner as in Example 1 were placed in a thermostat set at 40° C. and irradiated with UV light in the same manner as in Example 1 for 1000 hours. Meanwhile, the coated plates were taken out of the thermostat at appropriate time intervals, washed with water, and dried, and the 60° gloss was measured in the same manner as in Example 1. As a result, the coated plates showed no change of gloss from the initial value 94 until the end of the 1000-hour irradiation.

EXAMPLE 2

Figure 1:
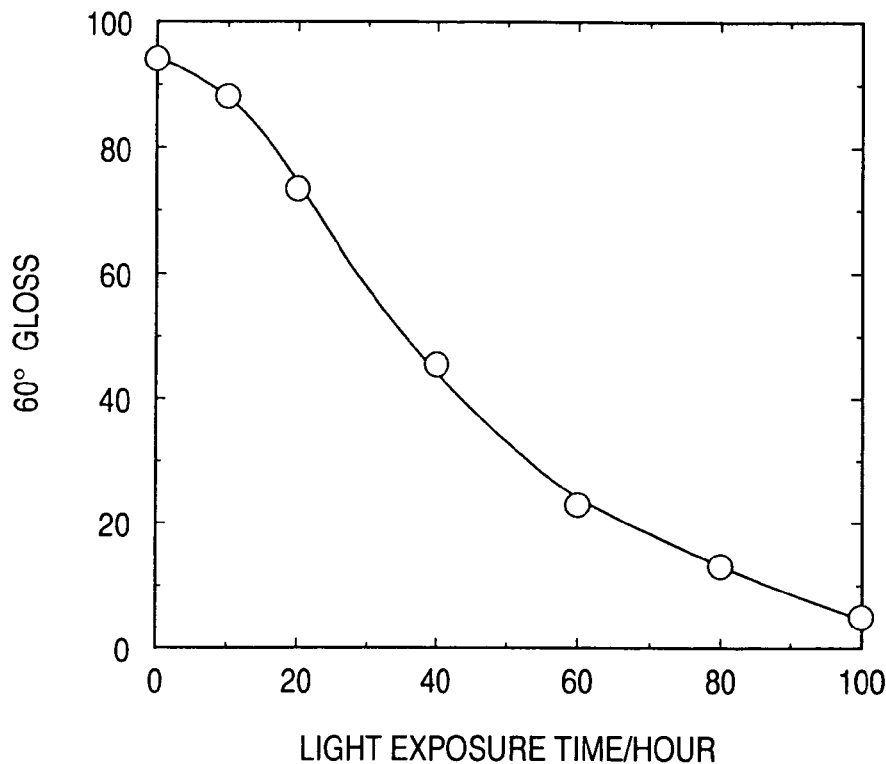
FIG. 1 is a graph showing the relationship between light exposure time and 60° gloss in Example 2.

A plurality of coated plates (3.5 cm×15 cm×0.8 mm) were prepared in the same manner as in Example 1. Each coated plate was put into a silica glass-made cylindrical container (43 mm in diameter; 200 mm in height, and 2 mm in wall thickness) together with about 150 ml of 3 wt % aqueous hydrogen peroxide, and the container was closed with a silicone rubber stopper. A plurality of the thus prepared containers having the coated plate and aqueous hydrogen peroxide therein were disposed in a thermostat kept at 40° C. in such a manner that the coated side of every plate might face a UV fluorescent lamp provided outside the thermostat about 60 mm away from the plate. The coated side of each plate was irradiated with light from the UV fluorescent lamp under the same conditions as in Example 1. Meanwhile, the coated plates were taken out of the thermostat at appropriate time intervals, washed with water, and dried, and the 60° gloss was measured in the same manner as in Example 1. The initial 60° gloss immediately after the preparation of the test pieces was 94, whereas the 60° gloss after 100-hour irradiation was 5. The plots of 60° gloss vs. irradiation time (light exposure time) are shown in FIG. 1.

COMPARATIVE EXAMPLE 2

The same weathering test as in Example 2 was carried on a plurality of coated plates (3.5 cm×15 cm×0.8 mm) prepared in the same manner as in Example 1, except for replacing the 3 wt % aqueous hydrogen peroxide with ion-exchanged water. As a result, the coated plates underwent no change of 60° gloss from the initial value 94 until 300 hours.

EXAMPLE 3

Figure 2:
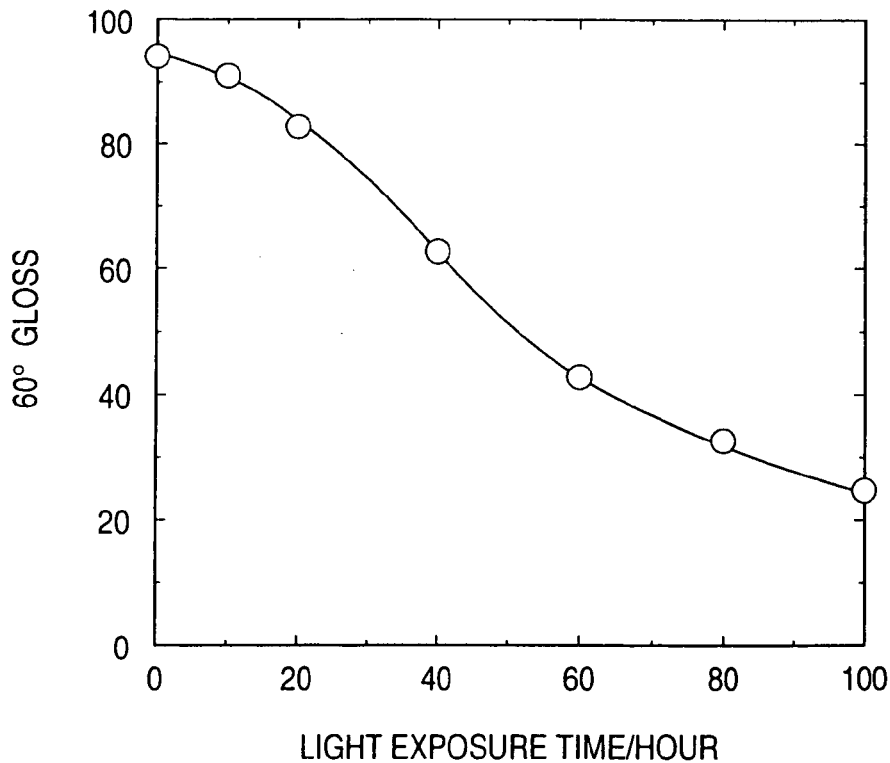
FIG. 2 shows the relationship between light exposure time and 60° gloss in Example 3.

A weathering test by irradiation was carried out in the same manner as in Example 2, except for replacing the 3 wt % aqueous hydrogen peroxide with 1 wt % aqueous solution of sodium peroxocarbonate. The results obtained are plotted in FIG. 2.

EXAMPLE 4

A weathering test using a sunshine weather meter (manufactured by Suga Test Instruments Co., Ltd.) was applied to a plurality of coated plates prepared in the same manner as in Example 1. The test was undertaken under standard conditions as specified except that highly pure water to be sprayed to give a water load was replaced with 0.01 wt % aqueous hydrogen peroxide. The coated plate was taken out to measure the 60° gloss at given time intervals in the same manner as in Example 2. The 60° gloss of the coated plate immediately after the preparation was 94, which decreased to 51 after 500 hours' testing. The plots of 60° gloss vs. testing time are shown in FIG. 3.

COMPARATIVE EXAMPLE 3

A plurality of coated plates prepared in the same manner as in Example 1 A were subjected to a weathering test using a sunshine weather meter (manufactured by Suga Test Instruments Co., Ltd.) under standard conditions as specified. The 60° gloss of the coated plates was measured in the same manner as in Example 4. The initial 60° gloss immediately after the preparation of the coated plate was 94, which decreased to 91 after 1000 hours' testing. The 60° gloss plotted against the testing time is shown in FIG. 4.

EXAMPLE 5

A coated plate prepared in the same manner as in Example 1 was immersed in 30 wt % aqueous hydrogen peroxide (a reagent available from Wako Pure Chemical Industries, Ltd.) at 20° C. for 30 minutes while shielded from light. The coated plate was taken out of the aqueous hydrogen peroxide and immediately washed with water for 5 seconds. The washed coated plate was set in a thermostat at 40° C. and irradiated with light from a UV fluorescent lamp placed about 60 mm away from the plate for 10 hours in the same manner as in Example 1. The 60° gloss of the coated plate immediately after the preparation was 94, which decreased to 88 after the irradiation.

COMPARATIVE EXAMPLE 4

A coated plate prepared in the same manner as in Example 1 was subjected to an outdoor exposure test in Okinawa, Japan for 24 months, and the 60° gloss of the coated side was measured every 3 months. The 60° gloss immediately after the preparation of the coated plate was 94, which decreased to 67 after 24 months' exposure. The plots of the 60° gloss against the exposure time are shown in FIG. 5.

Observations:

Comparison between Example 1 and Comparative Example 1 reveals that deterioration of a coating film by light can be accelerated by directly applying an active oxygen-releasing substance to the coated plate, whereby reduction in gloss of the coated plate can be reproduced in a shortened period of time. Further, Examples 2 and 3 in view of Comparative Example 2 show that immersion of the test piece in an aqueous solution of an active oxygen-releasing substance achieves reproduction of reduction in gloss in a short time.

It is seen by comparing Example 4 and Comparative Example 3 that deterioration of the coating film of a test piece by light is accelerated to reproduce reduction in gloss in a short time by spraying an aqueous solution of an active oxygen-releasing substance to the test piece. This result applies to conventional artificial accelerated weathering tests to increase the rate of acceleration of deterioration, thereby enhancing the usefulness of the weathering tests.

Comparative Example 4 is an outdoor weathering test relying on exposure to natural weathering conditions. The time required for the coated plate to reduce its 60° gloss to 90 is 12 months in this outdoor weathering, whereas it is 8 hours in Example 2, 12 hours in Example 3, 160 hours in Example 4, and 1000 hours in Comparative Example 3. Accordingly, the rate of deterioration in these Examples is 1100, 730, 55, and 8.8 times, respectively, that observed in the outdoor weathering test. From these rates of accelerated deterioration, it is understood that the weathering test according to the first aspect of the invention achieves remarkable acceleration of deterioration.

APPARATUS EXAMPLE 1

FIG. 6 illustrates an apparatus by which the first aspect of the present invention can be carried out easily. A test piece 15 is immersed in an aqueous solution 12 of an active oxygen-releasing substance and irradiated with UV light emitted from a light source 14 through an optical filter and the wall of a silica glass-made container 13. Since the silica glass container 13 is placed in a thermostat 11, the test piece 15 is kept at a prescribed temperature.

APPARATUS EXAMPLE 2

In FIG. 7 is shown another apparatus for suitably carrying out the weathering test according to the first aspect of the invention. The apparatus comprises a casing 21, a liquid pan 22, a holding member 23 which holds test pieces 25, and a light source 24. The casing 21 has a function as a thermostat. The liquid pan 22 is put on the bottom of the casing 21 and contains an aqueous solution of an active oxygen-releasing substance. The holding member 23 is positioned in the central portion of the casing 21 and is rotatable on a horizontal axis so that a lower part of the holding member 23 may successively be immersed in the aqueous solution in the pan 22. The holding member 23 is a rotatable cylindrical cage, and the test pieces 25 can be attached to the inner side of the cage with their side to be tested facing the center of the rotation. The light source 24 is set in the casing 21 at the center of the rotation of the holding member 23 so as to face every test piece 25.

The holding member 23 revolves on a horizontal axis at a constant speed by means of a driving mechanism not shown. The speed of revolution is adjustable in a range of from 1 to 100 revolutions per hour. Thus, each test piece 25 as attached to the holding member 23 revolves in the thermostat at a given speed and, meanwhile, intermittently immersed in the aqueous solution in the liquid pan 22 and constantly irradiated with light from the light source 24.

Each test piece 25 is always irradiated throughout a test cycle consisting of an immersed state in the aqueous solution, a wet state with the aqueous solution after emerging from the liquid pan 22, a state in which water is evaporated, and the active oxygen-releasing substance is concentrated and brought into contact with the surface of each test piece 25 or penetrating into the inside of the test piece 25, and a state until it is again immersed in the aqueous solution. The test piece 25 is repeatedly subjected to this test cycle. As a result, deterioration of each test piece 25 is accelerated efficiently.

EXAMPLE 6

A coated steel plate prepared in the same manner as in Example 1 was subjected to an outdoor exposure test in Aichi, Japan in accordance with the test method specified in JIS Z2381 except that 0.1 wt % aqueous hydrogen peroxide was sprayed once a day onto the coated surface of the plate under testing at noon for 10 seconds to wet the entire coated surface. Part of hydrogen peroxide sprayed penetrates inside the coating film and acts substantially together with light. The test was started in May and continued for 6 months. After completion of the testing, the 60° gloss of the coated plate was measured in the same manner as in Example 1, and the surface profile of the coating film was observed under a scanning electron microscope (SEM) JSM-890 (manufactured by JEOL Ltd.).

The 60° gloss was 94 immediately after the preparation of the coated plate and 75 after the 6 months' testing. The SEM observation revealed fine waviness and fine pits on the surface, which agreed with the surface profile characteristically observed in outdoor deterioration.

COMPARATIVE EXAMPLE 5

A plurality of coated plates prepared in the same manner as in Example 1 were subjected to an outdoor exposure test in accordance with the test method specified in JIS Z2381 concurrently with Example 6. The 60° gloss of the coated plate was measured at appropriate time intervals, and the surface profile of the coating film was observed at the same time in the same manner as in Example 6.

The 60° gloss after 6 months' exposure showed substantially no change from the initial value 94. Neither did the SEM observation revealed any change. When the outdoor exposure test was further continued for an additional 2 years and a half period (3 years in total), the 60° gloss was reduced to 80, and the surface profile showed fine waviness and fine pits in a mixed state.

EXAMPLE 7

A plurality coated plates (3.5 cm×15 cm×0.8 mm) prepared in the same manner as in Example 1 were immersed in warm water at 80° C. for 24 hours and then each put into a silica glass-made cylindrical container (43 mm in diameter; 200 mm in height, and 2 mm in wall thickness) together with about 150 ml of 3 wt % aqueous hydrogen peroxide, and each container was closed with a silicone rubber stopper. The containers were set upright in a thermostat kept at 40° C. with the coated side of each coated plate facing a UV fluorescent lamp which was placed about 60 mm away from the coated surface, and irradiated with light from the lamp. An optical filter made of glass was placed between the container and the light source so that the light reaching the coated plate might have wavelengths of 295 to 400 nm.

During the testing, the coated plates were taken out of the container at appropriate time intervals, and the 60° gloss was measured in the same manner as in Example 1. After 50 hours' testing, the surface profile of the irradiated coating film was observed. The initial 60° gloss immediately after the preparation of the coated plate was 94, whereas the 60° gloss after 50-hour irradiation was 40. The plots of 60° gloss vs. irradiation time (light exposure time) are shown in FIG. 8. The SEM observation revealed fine waviness and fine pits in a mixed state on the surface, which agreed with the surface profile characteristically observed in outdoor deterioration.

COMPARATIVE EXAMPLE 6

The same weathering test as in Example 7 was carried on a plurality of coated plates (3.5 cm×15 cm×0.8 mm) prepared in the same manner as in Example 1, except for replacing the 3 wt % aqueous hydrogen peroxide with ion-exchanged water. The initial 60° gloss immediately after the preparation of the coated plate was 94, whereas that after 50-hour irradiation was 89. Under SEM observation, fine waviness was slightly observed but with no fine pits characteristic of outdoor deterioration.

COMPARATIVE EXAMPLE 7

The same weathering test as in Example 7 was carried on a plurality of coated plates (3.5 cm×15 cm×0.8 mm) prepared in the same manner as in Example 1, except that the immersion in 80° C. warm water was not conducted. After 50 hours' irradiation, the 60° gloss was 58, and the surface profile under SEM observation displayed fine pits characteristic of outdoor deterioration but no fine waviness, another characteristic of outdoor deterioration.

EXAMPLE 8

A coated plate (3.5 cm×15 cm×0.8 mm) prepared in the same manner as in Example 1 was subjected to 5 cycles of weathering treatments in accordance with the diagram shown in FIG. 9. Each cycle consisted of:

treatment 1 in which the coated plate was immersed in deionized water in a thermostat set at 60° C. for 6 hours, treatment 2 in which the coated plate taken out of the deionized water was put in a silica glass-made container (43 mm in diameter; 200 mm in height, and 2 mm in wall thickness) together with about 150 ml of 0.5 wt % aqueous hydrogen peroxide, the container closed with a silicone rubber stopper and set in a thermostat at 60° C. a wall of which was made of a glass filter, and the coated side of the plate irradiated with light from a UV fluorescent lamp for 3 hours through the glass filter and the wall of the silica glass-made container, and treatment 3 in which the aqueous hydrogen peroxide was discharged from the silica glass container, the container was rinsed with deionized water, all the deionized water but about 2 ml was discharged, the container was again closed with a silicone rubber stopper, and the coated plate in the container was irradiated for 15 hours under the same conditions as in treatment 2.

Treatment 1 corresponds to a step B, treatment 2 to step A, and treatment 3 to another step B which is carried out in the same silica glass container as used in treatment 2 except that the inside of the container was kept in a high humidity atmosphere.

The 60° gloss of the coating film was measured in the same manner as in Example 1 at every end of one cycle. The surface profile of the coating film was observed under SEM at the end of 5 cycles. The relationship between 60° gloss and the number of cycles is shown in FIG. 10.

As is seen from FIG. 10, the 60° gloss, which was 94 immediately after the preparation of the coated plate, was reduced to 30 after 5 cycles of treatments. The surface profile after 5 cycles revealed a mixed state of fine waviness and fine pits, which was in good agreement with the conditions characteristic of outdoor deterioration.

EXAMPLE 9

A sunshine weather meter (Suga Test Instruments Co., Ltd.) was modified to have another spray unit in addition to the spray unit for applying highly pure water. A plurality of coated plates (3.5 cm×15 cm×0.8 mm) prepared in the same manner as in Example 1 were set in the modified sunshine weather meter and tested under the standard conditions as specified for a standard sunshine weather meter, except that loading with a spray of highly pure water was preceded by loading with a 10-minute spray of 0.01 wt % aqueous hydrogen peroxide from the additional spray unit along with irradiation. The coated plates were taken out at given time intervals to measure the 60° gloss in the same manner as in Example 1. Further, the surface profile of the coating film after 500-hour testing was observed in the same manner as in Example 6. The plots of 60° gloss against the testing time are depicted in FIG. 11.

As can be seen from FIG. 11, the 60° gloss, which was initially 94, reduced to 52 after 500-hour testing. The SEM observation revealed a mixed state of fine waviness and fine pits on the surface, which agreed with the state characteristic of outdoor deterioration.

Comparative Example 8

A plurality of coated plates (3.5 cm×15 cm×0.8 mm) prepared in the same manner as in Example 1 were tested in the same sunshine weather meter (unmodified) as used in Example 9 for 1200 hours under the standard conditions as specified. The coated plates were taken out at given time intervals to measure the 60° gloss, and the surface profile of the coating film after 1200-hour testing was observed in the same manner as in Example 6. The plots of 60° gloss against the testing time are depicted in FIG. 12.

As is shown in FIG. 12, the 60° gloss, which was initially 94, reduced to 90 after 1200-hour testing. The SEM observation revealed slight fine waviness but no fine pits which are characteristic of outdoor deterioration.

EXAMPLE 10

A coated plate (3.5 cm×15 cm×0.8 mm) prepared in the same manner as in Example 1 was subjected to the same weathering test as in Example 6, except for replacing the aqueous hydrogen peroxide with a 0.25 wt % aqueous solution of chlorine. As a result, the 60° gloss, which was initially 94, reduced to 85 after the 6-month testing. The surface profile under SEM had fine waviness and fine pits and agreed with that observed characteristically in outdoor deterioration.

Observations:

Comparative Example 5 consists of only step B of the two essential steps involved in the second aspect of the invention. Example 6 is a combination of the step B of Comparative Example 5 and step A in which the surface of the coated plate is wetted with aqueous hydrogen peroxide. Obviously, deterioration by outdoor exposure is accelerated in Example 6.

Comparative Example 6 is the same as in Example 7 except for replacing UV irradiation in aqueous hydrogen peroxide (step A in Example 7) with UV irradiation in pure water (corresponding to step B in Example 7). That is, Comparative Example 6 practically consists of only step B. On the other hand, Comparative Example 7 presents omission of the immersion in warm water from Example 7 and consists of only step A. No fine pits characteristic of outdoor deterioration was observed in Comparative Example 6 (only step B), and no fine waviness also characteristic of outdoor deterioration was observed in Comparative Example 7 (only step A). To the contrary, the coated plate tested in Example 7 revealed both fine pits and fine waviness, demonstrating highly accurate reproduction of outdoor deterioration.

Example 8 shows testing equipment and procedures for efficiently reproducing the aging of a material attending outdoor exposure by repetition of a combination of step A and step B.

In Example 9 is demonstrated an embodiment in which an available accelerated weathering apparatus was slightly modified so as to serve for the weathering test according to the second aspect of the invention thereby to produce the effects as intended. In this modified apparatus, aqueous hydrogen peroxide is sprayed to the coated plate while irradiated to embody step A, and the situation with no spray of aqueous hydrogen peroxide corresponds to step B. By use of the modified apparatus steps A and B can be performed successively and/or alternately. Compared with Comparative Example 8, it is obvious that Example 9 achieves the effects as intended in the invention.

Example 10 displays use of an oxidizing agent causing an element other than oxygen to act in step A. On comparing with the results of Comparative Example 5, it is apparent that the effects as aimed in the invention can be accomplished with such an oxidizing agent as well.

While the invention has been described in detail and with reference to specific examples thereof, it will be apparent to one skilled in the art that various changes and modifications can be made therein without departing from the spirit and scope thereof.

What is claimed is:

1. A weathering apparatus comprising:
   a container for holding a test piece;
   means for simultaneously making light and an aqueous solution of an oxidizing agent act on the test piece wherein the oxidizing agent has a concentration of from 0.01 to 10 percent by weight, wherein the oxidizing agent comprises at least one member selected from the group consisting of hydrogen peroxide, peracids, peracid salts, hypohalogenous acids, and hypohalogenous acid salts.

2. The weathering apparatus of claim 1, wherein said means comprises at least one light source selected from the group consisting of a xenon lamp, a metal halide lamp, a carbon arc lamp, an ultraviolet fluorescent lamp, and sunlight.

3. The weathering apparatus of claim 1, wherein said means comprises at least one of means for immersing the test piece in an aqueous solution of the oxidizing agent and means for spraying an aqueous solution of the oxidizing agent on the test piece.

4. The weathering apparatus of claim 1, wherein:
said container is equipped with a light-transmitting wall; and
said means comprises a means for making light act on the test piece, and said means for making light act is provided outside the container.

5. The weathering apparatus of claim 1, wherein said means comprises means for making light act on the test piece, and said means for making light act is provided inside the container.

6. The apparatus of claim 1, wherein the apparatus holds at least one test piece selected from the group consisting of an organic material, an article comprising an organic material, and an article coated with an organic material.

7. The apparatus of claim 1, wherein the oxidizing agent is hydrogen peroxide.

8. The apparatus of claim 1, wherein said means comprises a spray unit for spraying an aqueous solution of the oxidizing agent on the test piece.

9. A weathering test method comprising:
carrying out a weathering test with the weathering apparatus of claim 1.

10. The weathering apparatus of claim 1, wherein the oxidizing agent comprises hydrogen peroxide.

11. A weathering apparatus comprising:
a container for holding a test piece;
means for simultaneously making light and an aqueous solution of an oxidizing agent act on the test piece, wherein the oxidizing agent has a concentration of from 0.01 to 10 percent by weight; and
means for making at least one of light, oxygen and water act on the test piece,
wherein the oxidizing agent comprises at least one member selected from the group consisting of hydrogen peroxide, peracids, peracid salts, hypohalogenous acids, and hypohalogenous acid salts.

12. The weathering apparatus of claim 11, wherein said means for simultaneously making light and an aqueous solution of an oxidizing agent act comprises at least one light source selected from the group consisting of a xenon lamp, a metal halide lamp, a carbon arc lamp, an ultraviolet fluorescent lamp, and sunlight.

13. The weathering apparatus of claim 11, wherein said means for simultaneously making light and an aqueous solution of an oxidizing agent act comprises at least one of means for immersing the test piece in an aqueous solution of the oxidizing agent and means for spraying an aqueous solution of the oxidizing agent on the test piece.

14. The weathering apparatus of claim 11, wherein:
said container is equipped with a light-transmitting wall; and
said means for simultaneously making light and an aqueous solution of the oxidizing agent act comprises a means for making light act on the test piece, and said means for making light act is provided outside the container.

15. The weathering apparatus of claim 11, wherein said means for simultaneously making light and an aqueous solution of the oxidizing agent act comprises a means for making light act on the test piece, and said means for making light act is provided inside the container.

16. The apparatus of claim 11, wherein the oxidizing agent is hydrogen peroxide.

17. The apparatus of claim 11, wherein said means for making light and an aqueous solution of an oxidizing agent act on the test piece comprises a spray unit for spraying an aqueous solution of the oxidizing agent on the test piece.

18. A weathering test method comprising:
carrying out a weathering test with the weathering apparatus of claim 11.

19. The weathering apparatus of claim 11, wherein the oxidizing agent comprises hydrogen peroxide.

* * * * *